United States Patent [19]

Miyake

[11] Patent Number: 5,772,298
[45] Date of Patent: Jun. 30, 1998

[54] HAND-HELD TYPE EYE EXAMINING APPARATUS, AUXILIARY APPARATUS ON WHICH THE HAND-HELD TYPE EYE EXAMINING APPARATUS IS MOUNTED, AND OPTHALMOLOGIC APPARATUS HAVING THE HAND-HELD TYPE EYE EXAMINING APPARATUS AND THE AUXILIARY APPARATUS

[75] Inventor: Nobuyuki Miyake, Hiratsuka, Japan

[73] Assignee: Nikon Corporation, Tokyo, Japan

[21] Appl. No.: 806,234

[22] Filed: Feb. 24, 1997

[30] Foreign Application Priority Data

Feb. 29, 1996 [JP] Japan ................................. 8-043017

[51] Int. Cl.⁶ .................................................. A61B 3/10
[52] U.S. Cl. .......................... 351/205; 351/200; 351/204
[58] Field of Search .................................. 351/200, 204, 351/205, 206, 245

[56] References Cited

U.S. PATENT DOCUMENTS

| 5,528,323 | 6/1996 | Fujieda et al. ............................ 351/218 |
| 5,565,939 | 10/1996 | Fujieda .................................... 351/205 |
| 5,612,754 | 3/1997 | Tanaka .................................. 351/205 X |

FOREIGN PATENT DOCUMENTS

| 0349228 | 1/1990 | European Pat. Off. ................ 351/200 |
| 2-5920 | 1/1990 | Japan . |
| 4-73046 | 3/1992 | Japan ...................................... 351/200 |

OTHER PUBLICATIONS

Patent Abstracts of Japan, vol. 18, No. 451 (C–1241), Aug. 23, 1994 (JP–A–06 142 057).
Patent Abstracts of Japan, vol. 95, No. 3, Apr. 28, 1995 (JP–A–06 339 465).

Primary Examiner—Huy Mai
Attorney, Agent, or Firm—Shapiro and Shapiro

[57] ABSTRACT

An ophthalmologic apparatus comprises an eye examining apparatus of the hand-held type, an auxiliary apparatus on which the eye examining apparatus is removably mounted, a discrimination circuit for discriminating whether the eye examining apparatus and the auxiliary apparatus are connected together or separated from each other, and a controller for operatively associating the eye examining apparatus and the auxiliary apparatus with each other when the discrimination circuit discriminates that the eye examining apparatus is connected.

17 Claims, 5 Drawing Sheets

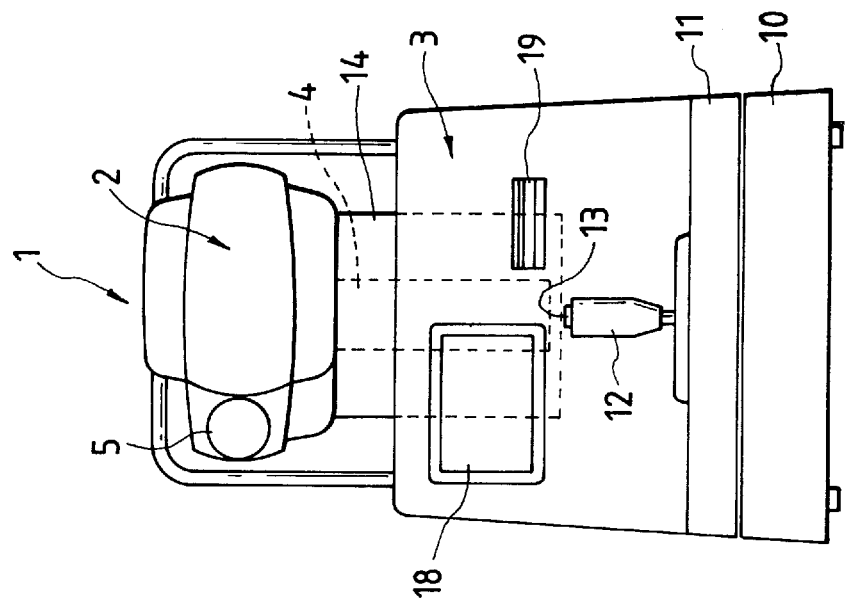
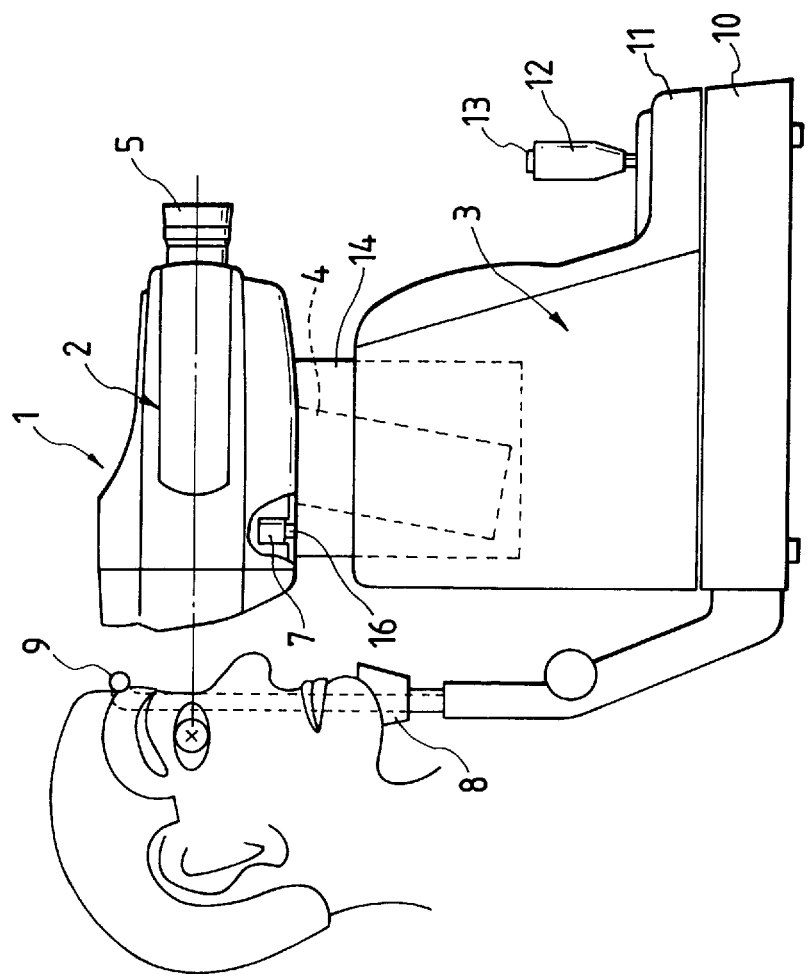
FIG. 1A
FIG. 1B

HAND-HELD TYPE EYE EXAMINING APPARATUS, AUXILIARY APPARATUS ON WHICH THE HAND-HELD TYPE EYE EXAMINING APPARATUS IS MOUNTED, AND OPTHALMOLOGIC APPARATUS HAVING THE HAND-HELD TYPE EYE EXAMINING APPARATUS AND THE AUXILIARY APPARATUS

The entire disclosure of Japanese Patent Application No. 8-43017 including specification, claims, drawings and summary is incorporated herein by reference in its entirety.

BACKGROUND OF THE INVENTION

1. Field of the Invention

This invention relates to an ophthalmologic apparatus for use for the examination of eyes in ophthalmic hospitals, opticians' stores, etc., and particularly to an ophthalmologic apparatus in which a hand-held type eye examining apparatus can be used also as an installation type.

2. Related Background Art

Ophthalmologic apparatuses according to the prior art include the installation type ones and the hand-held type ones. The installation type is a type in which an examinee's chin and brow are fixed to thereby fix the examinee's eyes and an apparatus is moved to right and left and back and forth, whereby the alignment between the apparatus and an eye to be examined is effected. The hand-held type is a type in which without an examinee's head being fixed, alignment is effected with an apparatus moved freely.

An autorefractometer 100 of the installation type which is a typical ophthalmologic apparatus will hereinafter be described with reference to FIGS. 4A and 4B of the accompanying drawings.

The autorefractometer is an apparatus for measuring the refractive power of an eye. This autorefractometer 100 fixes the face of an examinee 200 by his chin being placed on a chin receiver 101 and his brow being applied to a brow pad 102.

Further in this state, the examinee 200 looks at a target for fixation within the measuring portion 103 of the autorefractometer 100, whereby the stability of an eye 201 to be examined is secured. The measuring portion 103 is mounted on a slidable stand 105. By an operating stick 106 being brought down back and forth and to right and left, the slidable stand 105 can be moved back and forth and to right and left relative to a base 104. Further, by the operating stick 106 being rotated, the measuring portion 103 can be moved up and down relative to the slidable stand 105.

A measurement starting switch 107 for starting measurement is provided on top of the operating stick 106.

An examiner can observe the state of the eye 201 to be examined by means of a monitor 108 belonging to the slidable stand 105. By the slidable stand 105 being moved back and forth and to right and left and up and down, alignment is adjusted so that the optical axis of the measuring portion 103 and the eye 201 to be examined may coincide with each other. After the completion of the adjustment of the alignment, the examiner depresses the measurement starting switch 107 to thereby start measurement. The adjustment of the alignment and the measurement are effected for each eye.

After the termination of the measurement, the result of the measurement is printed by a printer 109.

An autorefractometer of the hand-held type will now be described with reference to FIG. 5 of the accompanying drawings.

The great difference of the autorefractometer of the hand-held type from the autorefractometer of the installation type is that the former is not provided with the brow pad and chin receiver for fixing the position of the eye 201 to be examined and the face of the examinee 200 cannot be fixed and therefore eye examination in a free posture can be effected. The examiner 202 moves an autorefractometer 110 in accordance with the posture of the examinee 200 to thereby adjust alignment. The examiner 202 holds the grips 111 of the autorefractometer 110 by one of his hands and looks into a viewfinder 112, whereby be can adjust alignment while looking at an image similar to that on the monitor of the installation type autorefractometer. After the adjustment of the alignment, the examiner operates a measurement starting switch 113, whereby measurement is started. As a matter of course, it is necessary that the apparatus of the hand-held type be made compact and light in weight sufficiently to such a degree that it can be operated by one hand.

One of autorefractometers of such hand-held type is described in Japanese Laid-Open Patent Application No. 2-5920. This example is such that only the measuring portion thereof is held by one hand, and is connected to the other portions of the apparatus by a cord.

The above-described apparatus of the hand-held type is great in its portability and degree of freedom of operation. On the other hand, however, the examinee's eyes are not fixed, and this has led to the problem that alignment is difficult to do as compared with the installation type. There has also been the problem that even if alignment is once done, it deviates very soon.

On the other hand, the installation type can stabilize the examinee's face and can fix his eyes, but depending on the examinee, there have been cases where eye examination cannot be accomplished. For example, young children, old people and users of wheeled chairs find it difficult to place their chins on the chin receiver and cannot sometimes be subjected to measurement. Also, to move the slidable stand greatly, the entire apparats must be moved, and the time required for measurement has been liable to become long. However, with regard to ordinary examinees, the installation type is easier in measurement.

As described above, the hand-held type and the installation type have their own merits and demerits, and to cope with all examinees, it has been preferable to be equipped with apparatuses of the both types. However, it has meant a great burden in cost to eye doctors, etc. to get two types of apparatuses having the same function.

SUMMARY OF THE INVENTION

It is the object of the present invention to solve the above-noted problems peculiar to the prior art and to provide an ophthalmologic apparatus which can be used properly as the hand-held type and the installation type as required.

The object of the present invention is achieved by an ophthalmologic apparatus having an eye examining apparatus of the hand-held type for measuring an eye to be examined, an auxiliary apparatus on which the eye examining apparatus is removably mounted, a discrimination circuit for discriminating whether the eye examining apparatus and the auxiliary apparatus are connected to each other or separated from each other, and a controller for operatively associating the eye examining apparatus and the auxiliary apparatus with each other when it is discriminated by the discrimination circuit that the eye examining apparatus is connected.

Also, the object of the present invention is achieved by a hand-held type eye examining apparatus having a measuring portion for measuring an eye to be examined, a first measurement switch for instructing the measuring portion to start measurement, a mounting mechanism for removably mounting the eye examining apparatus on an auxiliary apparatus placed at a predetermined position, and a controller for starting measurement on the basis of the instructions of a second measurement switch the auxiliary apparatus has when the eye examining apparatus is mounted on the auxiliary apparatus, and starting measurement on the basis of the instructions of the first measurement switch when the eye examining apparatus is separated from the auxiliary apparatus placed at the predetermined position.

Further, the object of the present invention is achieved by an auxiliary apparatus on which is removably mounted a hand-held type eye examining apparatus having a mounting mechanism on which is mounted the hand-held type eye examining apparatus provided with a first measurement switch for instructing the eye examining apparatus to start the measurement of an eye to be examined, and a second measurement switch for instructing the eye examining apparatus to start measurement when the hand-held type eye examining apparatus is mounted.

There is provided an ophthalmologic apparatus comprising an auxiliary unit used while being installed, and a hand-held unit used while being separated from or made integral with the auxiliary unit, the hand-held unit having a first mounting mechanism for making the hand-held unit integral with the auxiliary unit, a measuring unit for effecting a predetermined measuring process, and a data output portion for outputting the result of the measurement by the measuring unit to the auxiliary unit, the auxiliary unit having a second mounting mechanism mounted on the first mounting mechanism of the hand-held unit, a data input portion connected to the data output portion, a sliding unit for sliding the hand-held unit made integral with the auxiliary unit, an instructing portion for instructing the measuring unit of the hand-held unit to start measurement, and at least one of printing unit and display means for outputting the result of the measurement inputted through the data input portion.

When the hand-held unit is made integral with the auxiliary unit (auxiliary apparatus), the starting switch of the auxiliary unit receives the instructing operation for measurement start by a user and outputs an instruction signal for measurement start through an instruction output portion. Thereupon, the control unit of the hand-held unit (ophthalmologic apparatus) receives this instruction signal for measurement start through an instruction input portion and causes the measuring unit to start measurement in accordance therewith. Also, an examiner changes the position of the hand-held unit on the auxiliary unit by the sliding unit as required. The result of the measurement is inputted to the data input portion of the auxiliary unit through the data output portion. The printing unit (or display unit) of the auxiliary unit outputs the result of the measurement inputted through the data input portion. Further, the right and left eyes determining means of the auxiliary unit determines whether the eye to be measured is the right eye or the left eye. Also, an inter-pupil distance calculating unit finds the distance between the pupils.

In this case, the power control unit of the hand-held unit operates the measuring portion by electric power supplied by the power supplying unit of an installed unit through a power output portion and a power input portion.

On the other hand, when the hand-held unit is separated from the auxiliary unit, the power control unit operates the measuring portion by electric power stored in a battery.

As described above, according to the present invention, the forms of use of both the hand-held type and the installation type can be adopted and therefore, optimum eye examination can be effected in accordance with patients. Also, it becomes unnecessary for eye doctors, etc. to prepare a plurality of ophthalmologic apparatuses having the same function, and this mitigates the burden in cost.

BRIEF DESCRIPTION OF THE DRAWINGS

FIG. 1A is a side view of an autorefractometer 1 which is a first embodiment of the present invention.

FIG. 1B is a front view of the autorefractometer 1 which is the first embodiment of the present invention.

DESCRIPTION OF THE PREFERRED EMBODIMENTS

A first embodiment of the present invention will hereinafter be described with reference to the drawings.

Figure 2:
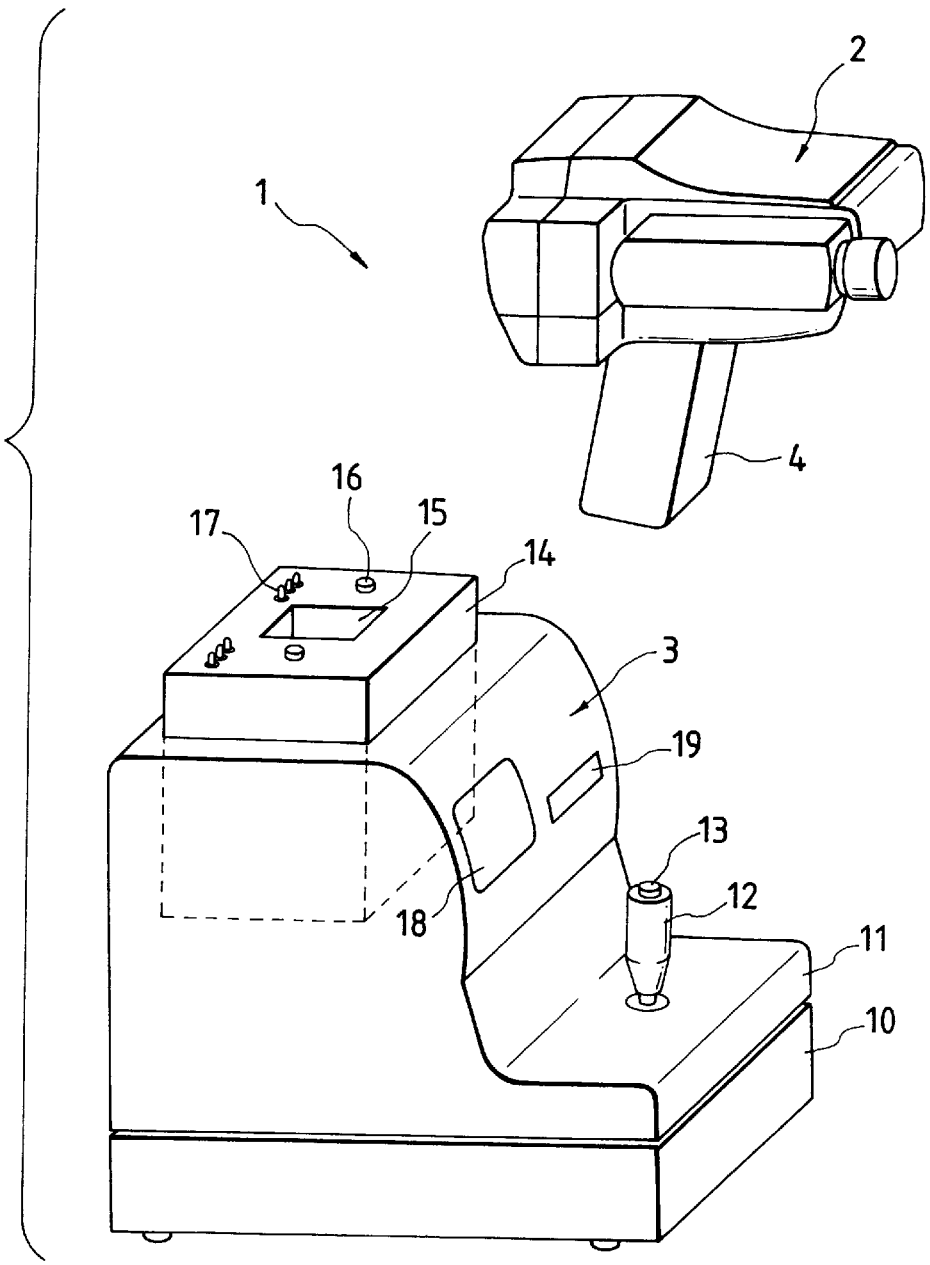
FIG. 2 is a perspective view showing a hand-held portion 2 and a dock 3 as they are separated from each other.

An autorefractometer 1 according to this embodiment is designed to be separable into a hand-held portion 2 and a dock 3 placed or a table or the like, as shown in FIGS. 1A, 1B and 2. The two are separated from each other or mounted on each other to thereby make measurement in two different forms of use possible. That is, the hand-held portion 2 is provided with each mechanism (e.g. a viewfinder 5) necessary for measurement and a battery, and is capable of effecting the measurement of an eye to be examined as a hand-held type autorefractometer. Further, by this hand-held portion 2 being mounted on and made integral with the dock 3, measurement similar to that by the conventional installation type is possible.

The present embodiment will hereinafter be described in detail.

As already described, the autorefractometer 1 according to the present embodiment can be broadly divided into the hand-held portion 2 and the dock 3. The internal construction of the autorefractometer 1 is shown in FIG. 3.

The hand-held portion 2 will first be described.

Figure 3:
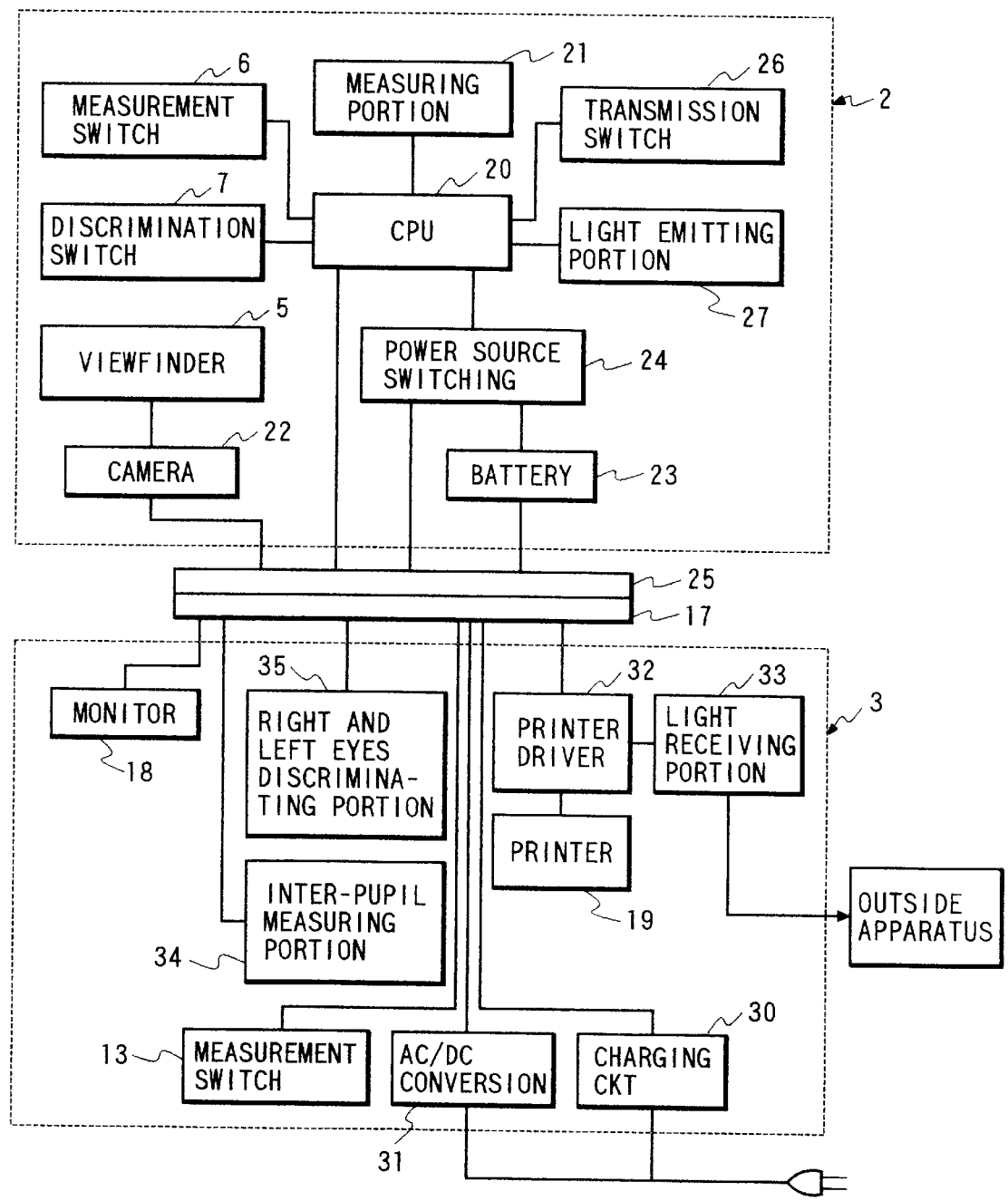
FIG. 3 is a block diagram showing the internal construction of the autorefractometer 1.
Figure 4A:
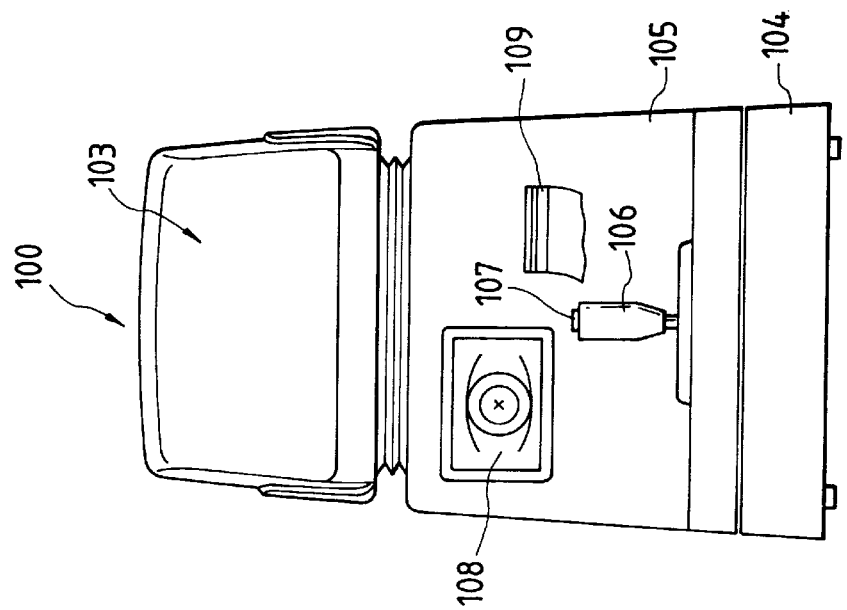
FIG. 4A is a side view of an autorefractometer of the installation type according to the prior art.
Figure 4B:
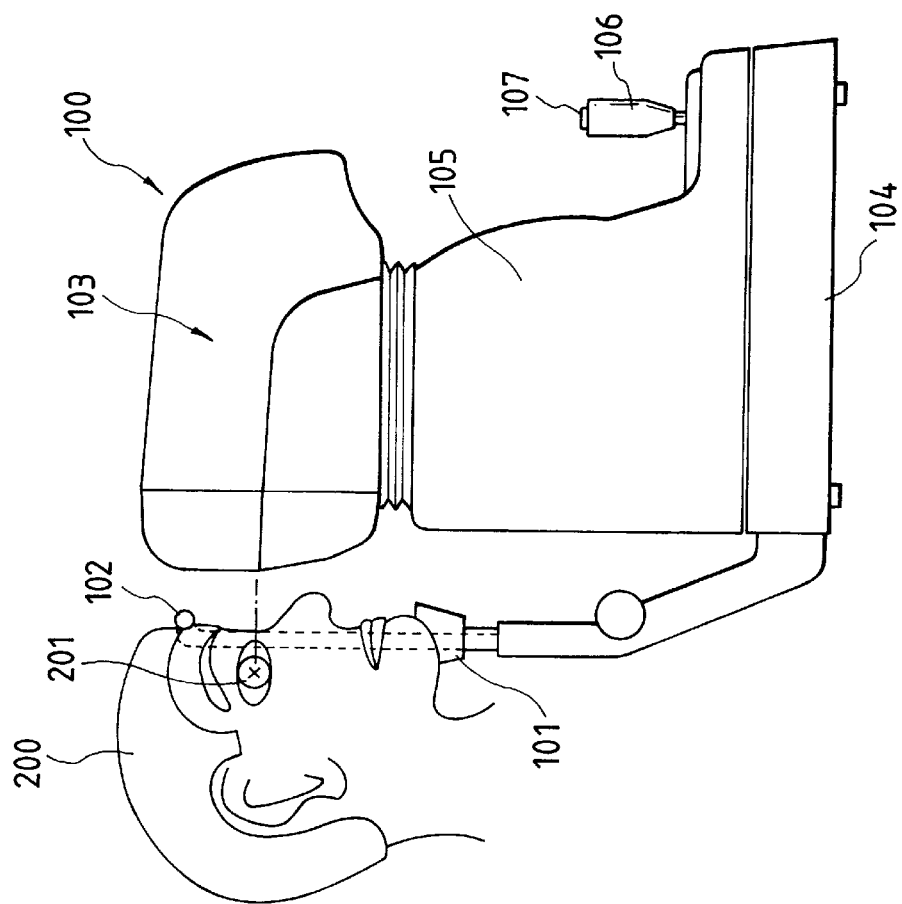
FIG. 4B is a front view of the autorefractometer of the installation type according to the prior art.
Figure 5:
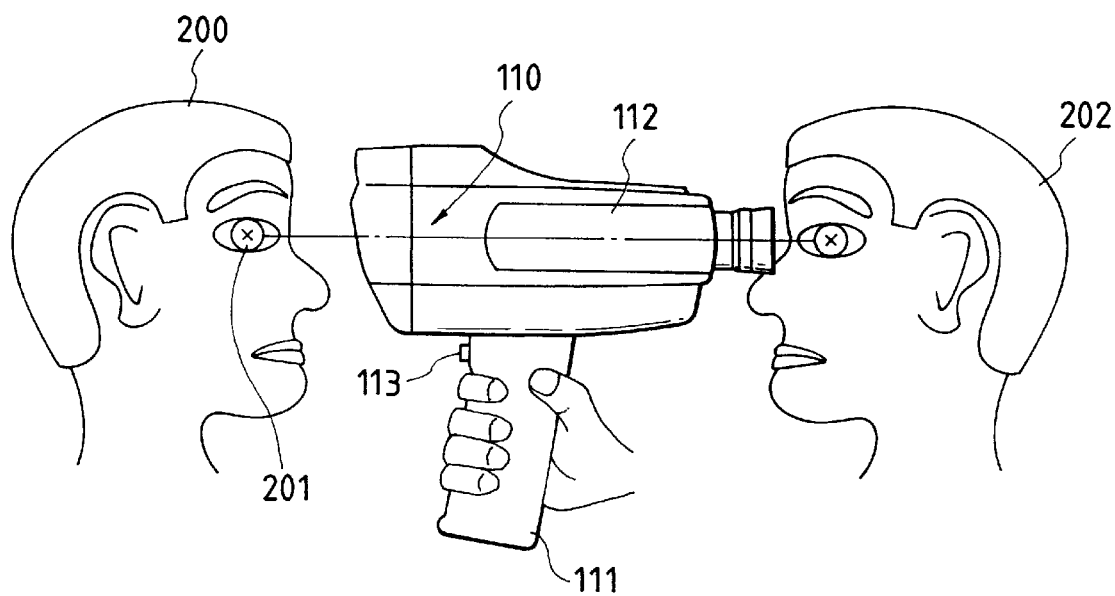
FIG. 5 shows a state in which an autorefractometer of the hand-held type is used.

The hand-held portion 2, as shown in FIG. 3, is provided with a measurement starting switch 6, a discrimination switch 7, a control portion 20, a measurement portion 21, a camera 22, an internal battery 23, a power source switching control portion 24, a contact group 25, a transmission switch 26 and a light emitting portion 27.

The discrimination switch 7 is for detecting the then form of use (i.e., whether the hand-held portion 2 is mounted on the dock 3). In the present embodiment, this discrimination switch 7 is provided on the underside of the housing of the hand-held portion 2 (see FIGS. 1A and 1B). In a state in which the hand-held portion 2 is separated from the dock 3, the discrimination switch 7 is in a state in which it protrudes the underside of said housing. Design is made such that when the hand-held portion 2 is mounted on and made integral with the dock 3, said protruding portion strikes against and is pushed in by an aligning pin 16 on the upper edge portion of a mounting portion 14 which will be described later, whereby the fact that the hand-held portion is in its mounted state is detected. The result of the detection by the discrimination switch 7 is outputted to the control portion 20.

The discrimination switch 7 serves to detect whether the hand-held portion 2 is mechanically mounted on the dock 3.

The control portion 20 serves to control the whole of this autorefractometer 1. This control portion 20 changes instructions for control in conformity with the result of the detection by the discrimination switch 7, and changes the operative state of each portion. Further, the control portion 20 changes the operative state of each portion also by inputting or ignoring the output signal from each portion. The detailed substance of the change will be described later in the description of each portion. The actual control portion 20 is comprised of a CPU, a memory and a control program stored in the memory.

The power source switching control portion 24 is for switching the power source of the hand-held portion 2 in conformity with the form of use. In a state in which the hand-held portion 2 alone is singly used, the power source switching control portion 24 supplies each portion with electric power stored in the internal battery 23. On the other hand, in a state in which the hand-held portion 2 is mounted on the dock 3, electric power supplied from the dock 3 through contact groups 17 and 25 is supplied to each portion. In this case, the charging of the internal battery 23 is also effected. However, the power source switching control portion 24 itself does not discriminate between the forms of use, but actually the substance of operation is adapted to be switched in accordance with the instructions from the control portion 20. In FIG. 3, the wiring for supplying electric power from the internal battery 23 to each portion is not shown.

The measuring portion 21 is a functional portion which effects various kinds of measurement. This measuring portion 21 starts measurement in accordance with the instructions from the control portion 20 inputted on the basis of the operation of the measurement starting switch 6 (or the measurement start switch 13 of the dock 3). Also, it is designed to output the result of the measurement to the control portion 20. However, in a form in which the hand-held portion 2 is mounted on the dock 3, the control portion 20 is designed to receive only the operation input of the measurement starting switch 13. Accordingly, in this state, measurement will not be started even if the measurement starting switch 6 is operated.

The light emitting portion 27 serves to output the result of the measurement by the measuring portion 21 as an optical signal. The light emitting portion 27 is adapted to output an optical signal indicative of the result of the measurement in accordance with the instructions from the control portion 20 inputted with the operation of the transmission switch 26 as a moment. It is supposed that this optical signal is received by the light receiving portion 33 of the dock 3. However, it is only when the hand-held portion 2 is separated from the dock 3 that the light emitting portion 27 is used. Design is made such that when the hand-held portion 2 is mounted on the dock 3, the result of the measurement is outputted to the dock 3 by the control portion 20 through the contact groups 25 and 17.

The camera 22 is for photographing the eye to be examined. In a state in which the hand-held portion 2 is separated from the dock 3, the camera 22 outputs its image pickup signal to the viewfinder 5. On the other hand, in a state in which the hand-held portion 2 is mounted on the dock 3, the camera 22 outputs its image pickup signal to a monitor 18 provided in the dock 3 through the contact groups 25 and 17.

The contact group 25 is for effecting the giving and receiving of various signals between the hand-held portion 2 and the dock 3, and the supply of electric power, as already described The dock 3 will now be described.

The dock 3 is provided with a mounting portion 14, a guide hole 15, the aligning pin 16 and the contact group 17 in appearance as mechanisms for mounting the hand-held portion 2 (see FIGS. 1A, 1B and 2). The dock 3 is similar to the sliding stand of the installation type according to the prior art in that it is provided with a base 10, a sliding stand 11, an operating stick 12, etc. and the position of the sliding stand 11 on the base 10 is changeable in conformity with the operation of the operating stick 12. The dock 3 is also similar to the sliding stand of the installation type according to the prior art in that the position of the sliding stand 11 in the right to left direction is detectable.

The mounting portion 14 is provided on top of the sliding stand 11. The mounting portion 14 is provided with the guide hole 15 at the center thereof. Also, the aligning pin 16 and the contact group 17 are provided on the respective portions of the upper end surface of the mounting portion 14. The mounting of the hand-held portion 2 is done by inserting the grip thereof into the guide hole 15. In the mounted state of the hand-held portion 2, the aligning pin 16 fits into an alignment hole (not shown) formed in the underside of the hand-held portion 2, whereby the relative positional relation between the two may be reliably fixed. Also, in this mounted state, the contact group 17 and the contact group 25 of the hand-held portion 2 are adapted to contact with each other reliably so that electrical conduction between the two may be accomplished.

On the other hand, the dock 3, as shown in FIG. 3, is internally provided with a charging circuit 30, an AC/DC conversion circuit 31, a printer 19, a printer driver 32, a light receiving portion 33, a monitor 18, an inter-pupil distance measuring portion 34 and a right and left eyes discriminating portion 35.

The charging circuit 30 is for charging the internal battery 23 of the hand-held portion 2. In the state in which the hand-held portion 2 is mounted, the charging circuit 30 is adapted to be connected to the internal battery 23 through the contact groups 25 and 17.

The AC/DC conversion circuit 31 is for supplying electric power for operating the hand-held portion 2 in its mounted state. This AC/DC conversion circuit 31 is adapted to be connected to the power source switching control portion 24 through the contact groups 25 and 17.

The printer driver 32 and the printer 19 are for printing the result of the measurement. Also, the light receiving portion 33 are for receiving the optical signal emitted by the light emitting portion 27. When measurement is being effected by the hand-held portion 2 alone, the printer driver 32 causes the printer 19 to print the data received by the light receiving portion 33. On the other hand, when the hand-held portion 2 is mounted on the dock 3, the printer driver is adapted to cause the printer 19 to print data sent through the contact groups 25 and 17.

The measurement starting switch 113, as already described, is for an examiner to input the instructions for measurement start in the state in which the hand-held portion 2 is mounted.

The right and left eyes discriminating portion 35 is for discriminating whether the eye to be measured in the state in which the hand-held portion 2 is mounted is the right eye or the left eye. Also, the inter-pupil distance measuring portion 34 is for measuring the distance between the right and left eyes. The principles of discrimination and measurement are similar to those in the prior art. That is, the position of the sliding stand 11 in a state in which alignment has been adjusted is detected, and on the basis of on which of the right and left sides of the base 10 that position is, whether the eye to be measured is the left eye or the right eye is discriminated. Further, the difference between the position of the sliding stand 11 during the measurement of the left eye (the position after the adjustment of alignment) and the position of the sliding stand 11 during the measurement of the right eye (the position after the adjustment of alignment) is calculated to thereby find the distance between the pupils. The actual right and left eyes discriminating portion 35 and inter-pupil distance measuring portion 34 are comprised of a position detecting mechanism for the sliding stand 11, a memory holding the result of the detection therein, a processor for effecting calculation, etc.

The monitor 18 serves to display an image picked up by the camera 22. This image signal is adapted to be sent through the contact groups 25 and 17.

The movement of the sliding stand 11 by the operating stick 12 is adapted to be mechanically accomplished.

Operation will now be described.

The control portion 20 sequentially confirms in what state the hand-held portion 2 is, on the basis of the result of the detection by the discrimination switch 7.

When as a result of this confirmation, the hand-held portion 2 is separate from the dock 3, the control portion 20 instructs the power source switching control portion 24 to supply the electric power of the internal battery 23 to each portion. In response to this, the power source switching control portion 24 supplies the electric power of the internal battery 23 to each portion. In this case, the image picked up by the camera is displayed in the viewfinder 5. Accordingly, the examiner adjusts the alignment while looking at the image being displayed in the viewfinder 5. The method of adjusting the alignment is accomplished by moving the autorefractometer 1 itself in accordance with an examinee's posture or the like as in the hand-held type autorefractometer according to the prior art. Accordingly, there will be no problem even if the examinee is a young child whose chin does not reach the chin receiver 8.

After the adjustment of the alignment, the examiner operates the measurement starting switch 6. Thereupon, the control portion 20 instructs the measuring portion 21 to start measurement. In response to this, the measuring portion 21 starts measurement. When the transmission switch 26 is operated after the completion of the measurement by the measuring portion 21, the control portion 20 causes the light emitting portion 27 to output measurement data as an optical signal. When the light receiving portion 33 receives the optical signal, the printer driver 32 causes the printer 19 to print the data.

On the other hand, when the hand-held portion 2 is mounted on the dock 3, the control portion 20 instructs the power source switching control portion 24 to supply each portion with the electric power sent from the AC/DC conversion circuit 31. In response to this, the power source switching control portion 24 supplies each portion with the electric power sent from the AC/DC conversion circuit 31. In this case, the image picked up by the camera 22 is displayed on the monitor 18. Accordingly, the examiner adjusts the alignment while looking at the image being displayed on the monitor 18. The method of adjusting the alignment is accomplished by operating the operating stick 12 as in the installation type autorefractometer according to the prior art. Accordingly, when the examinee is an ordinary adult, the adjustment of the alignment can be done more quickly and more reliably than when alignment is effected by the hand-held portion 2 alone.

After the adjustment of the alignment, the examiner operates the measurement starting switch 13. The operation input of this measurement starting switch 13 is transmitted to the control portion 20 through the contact groups 17 and 25. Thereupon, the control portion 20 instructs the measuring portion 21 to start measurement. In response to this, the measuring portion 21 starts measurement. In this case, even if it detects the operation of the measurement starting switch 6, the control portion 20 ignores it.

Also, on the basis of the position of the sliding stand 11 at the point of time where at the measurement starting switch 13 has been operated, the right and left eyes discriminating portion 35 and the inter-pupil distance measuring portion 34 find whether the eye to be measured at that time is the right eye or the left eye, and the distance between the pupils. The results obtained are outputted to the control portion 20 through the contact groups 25 and 17.

When the transmission switch 26 is operated after the completion of the measurement by the measuring portion 21, the control portion 20 sends measurement data to the dock 3 through the contact groups 25 and 17 and causes the printer 19 to effect printing through the printer driver 32. In this case, the control portion 20 causes not only the result of the measurement by the measuring portion 21 but also the results of the measurement by the right and left eyes discriminating portion 35 and the inter-pupil distance measuring portion 34 to be outputted.

According to the above-described embodiment, two different forms of use are used properly in conformity with the constitution or the like of the examinee, whereby quick and reliable measurement can always be effected.

Also, the measurement of the distance between the pupils or the like is possible in the state in which the hand-held portion 2 is mounted on the dock 3.

In the above-described embodiment, the dock 3 is provided with a printer, a monitor, etc., but need not be provided with these. In such case, even when the hand-held portion is mounted on the dock 3, measurement is effected by the use of the viewfinder 5 possessed by the hand-held portion 2. Also, the hand-held portion is connected to a discretely prepared printer as required.

Of course, the result of the measurement may also be displayed on the monitor 18.

In the above-described embodiment, design is made such that the result of the measurement is transmitted at the point of time whereat the transmission switch 26 has been operated. Alternatively, however, design may be made such that when the measuring process is being carried out (or at a point of time whereat the measuring process has been terminated), the result of the measurement then obtained is automatically outputted.

Although not particularly described in the foregoing description, the confirmation of the connection between the contact group 25 and the contact group 17 may of course be effected.

As described above, the ophthalmologic apparatus of the present invention can adopt both of the forms of use as the hand-held type and the installation type and therefore can effect optimum eye examination in conformity with patients. Also, it becomes unnecessary for eye doctors or the like to prepare a plurality of ophthalmologic apparatuses having the same function and thus, the burden in cost is mitigated.

While in the present embodiment, the invention has been described with respect to an autorefractometer, the present invention may also be applied to an autokeratometer or a retinal camera for observing the image of the fundus of an eye.

What is claimed is:

1. An ophthalmologic apparatus comprising:
    an eye examining apparatus of the hand-held type;
    an auxiliary apparatus on which said eye examining apparatus is removably mounted;
    a discrimination circuit for discriminating whether said eye examining apparatus and said auxiliary apparatus are connected together or separated from each other; and
    a controller for operating associating said eye examining apparatus and said auxiliary apparatus with each other when said discrimination circuit discriminates that said eye examining apparatus is connected.

2. An ophthalmologic apparatus according to claim 1, wherein when said discrimination circuit discriminates that said eye examining apparatus is separated, said controller controls said eye examining apparatus so as to operate said eye examining apparatus singly.

3. An ophthalmologic apparatus according to claim 1, wherein said eye examining apparatus of the hand-held type has a measuring portion for measuring an eye to be examined, and a first measurement switch for instructing said measuring portion to start the measurement of said eye to be examined, said auxiliary apparatus has a second measurement switch for instructing said measuring portion to start the measurement of said eye to be examined when said eye examining apparatus is connected, and said controller controls said measuring portion so as to effect the measurement of said eye to be examined on the basis of the instructions of the second measurement switch of said auxiliary apparatus when said discrimination circuit discriminates that said eye examining apparatus is connected.

4. An ophthalmologic apparatus according to claim 3, wherein said eye examining apparatus of the hand-held type has an output terminal for outputting the result of the measurement of said eye to be examined, and a transmitting portion for converting the result of the measurement of said eye to be examined into an optical signal and transmitting it, said controller controls said eye examining apparatus so as to output said result of the measurement to said auxiliary apparatus through said output terminal when said discrimination circuit discriminates that said eye examining apparatus is connected, and so as to output said result of the measurement to said auxiliary apparatus through said transmitting portion when said discrimination circuit discriminates that said eye examining apparatus is separated, and said auxiliary apparatus has a printer for printing and outputting the result of the measurement outputted from said transmitting portion or said output terminal.

5. An ophthalmologic apparatus according to claim 1, wherein said eye examining apparatus of the hand-held type has a measuring portion for measuring an eye to be examined, and a battery for supplying electric power to said measuring portion, said auxiliary apparatus has a power source for supplying electric power, and said controller drives said measuring portion with the electric power supplied from said power source when said discrimination circuit discriminates that said eye examining apparatus is connected, and drives said measuring portion with the electric power supplied from said battery when said discrimination circuit discriminates that said eye examining apparatus is separated.

6. An ophthalmologic apparatus according to claim 5, wherein when said discrimination circuit discriminates that said eye examining apparatus is connected, said controller supplies electric power from said power source to said battery and effects the charging of said battery.

7. An ophthalmologic apparatus according to claim 1, wherein said eye examining apparatus of the hand-held type has a camera for picking up the image of an eye to be examined, and a first monitor for displaying the image of the eye to be examined picked up by said camera, said second auxiliary apparatus has a second monitor, and said controller causes said second monitor to display the image of said eye to be examined when said discrimination circuit discriminates that said eye examining apparatus is connected, and causes said first monitor to display the image of said eye to be examined when said discrimination circuit discriminates that said eye examining apparatus is separated.

8. An ophthalmologic apparatus according to claim 1, wherein said auxiliary apparatus has at least one of a right and left eyes discriminating device for discriminating whether an eye to be examined being measured by said eye examining apparatus when said eye examining apparatus is connected is the right eye or the left eye, and an inter-pupil distance detector for finding the distance between the pupils.

9. A hand-held type eye examining apparatus comprising
    a measuring portion for measuring an eye to be examined;
    a first measurement switch for instructing said measuring portion to start measurement;
    a mounting mechanism for removably mounting said eye examining apparatus on an auxiliary apparatus placed at a predetermined position; and
    a controller for starting measurement on the basis of the instructions of a second measurement switch of said auxiliary apparatus when said eye examining apparatus is mounted on said auxiliary apparatus, and starting measurement on the basis of the instructions of said first measurement switch when said eye examining apparatus is separated from said auxiliary apparatus.

10. A hand-held type eye examining apparatus according to claim 9, further comprising a discrimination circuit for discriminating whether said eye examining apparatus is connected to or separated from said auxiliary apparatus, and wherein said controller controls said eye examining apparatus so as to effect the measurement of said eye to be examined on the basis of the instructions of the second measurement switch of said auxiliary apparatus when said discrimination circuit discriminates that said eye examining apparatus is connected, and controls said eye examining apparatus so as to effect the measurement of said eye to be examined on the basis of the instructions of the first measurement switch of said eye examining apparatus when said discrimination circuit discriminates that said eye examining apparatus is separated.

11. A hand-held type eye examining apparatus according to claim 9, further comprising an output terminal for outputting the result of the measurement of said eye to be examined, and a transmitting portion for converting the result of the measurement of said eye to be examined into an optical signal and transmitting it, and wherein said controller causes said result of the measurement to be outputted to said auxiliary apparatus through said output terminal when said eye examining apparatus is mounted on said auxiliary apparatus, and causes said result of the measurement to be outputted through said transmitting portion when said eye examining apparatus is separated from said auxiliary apparatus.

12. A hand-held type eye examining apparatus according to claim 9, further comprising a battery for supplying electric power to said measuring portion, and wherein said controller supplies electric power from said auxiliary apparatus to said measuring portion when said eye examining apparatus is connected to said auxiliary apparatus, and supplies from said battery to said measuring portion when said eye examining apparatus is separated from said auxiliary apparatus.

13. A hand-held type eye examining apparatus according to claim 12, wherein said battery is charged with electric power supplied from said auxiliary apparatus when said eye examining apparatus is connected to said auxiliary apparatus.

14. An auxiliary apparatus on which a hand-held type eye examining apparatus is removably mounted comprising:

a mounting mechanism on which is mounted the hand-held type eye examining apparatus provided with a first measurement switch for instructing said eye examining apparatus to start the measurement of an eye to be examined; and a second measurement switch for instructing said eye examining apparatus to start the measurement when said hand-held type eye examining apparatus is mounted.

15. An auxiliary apparatus according to claim 14, further comprising an input terminal for inputting the result of the measurement of said eye to be examined outputted from the output terminal of said hand-held type eye examining apparatus, a signal receiving portion for receiving an optical signal indicative of the result of the measurement transmitted from the signal transmitting portion of said hand-held type eye examining apparatus, and a printer for printing and outputting the result of the measurement inputted from said input terminal or the result of the measurement received by said signal receiving portion.

16. An auxiliary apparatus according to claim 14, having at least one of a right and left eyes discriminating device for discriminating whether the eye to be examined being measured by said eye examining apparatus when said eye examining apparatus is connected is the right eye or the left eye, and an inter-pupil distance detector for detecting the distance between the pupils.

17. A hand-held type eye examining apparatus comprising:

a camera for photographing an eye to be examined;

a first monitor for displaying the image of the eye to be examined photographed by said camera;

a mounting mechanism for removably mounting said eye examining apparatus on an auxiliary apparatus placed at a predetermined position; and a controller for causing a second monitor of said auxiliary apparatus to display said image of the eye to be examined when said eye examining apparatus is mounted on said auxiliary apparatus, and causing said first monitor to display said image of the eye to be examined when said eye examining apparatus is separated from said auxiliary apparatus.

* * * * *